United States Patent [19]
Chan et al.

[11] Patent Number: 5,700,360
[45] Date of Patent: Dec. 23, 1997

[54] FLUOROELASTOMER GASKET FOR BLOOD SENSORS

[75] Inventors: Andy D. C. Chan, Franklin; Mark W. Boden, Millbury; John S. Benco, Holliston; Robert A. Bergquist, Middleboro; Donna S. Orvedahl, Medfield, all of Mass.

[73] Assignee: Chiron Diagnostics Corporation, E. Walpole, Mass.

[21] Appl. No.: 550,884

[22] Filed: Oct. 31, 1995

[51] Int. Cl.⁶ .................................... G01N 27/26
[52] U.S. Cl. .................. 204/400; 204/403; 204/409; 204/415; 422/68.1; 422/82.01; 422/82.02; 422/82.03
[58] Field of Search ................... 204/400, 403, 204/415, 409, 421; 422/68.1, 82.01, 82.02, 82.03

[56] References Cited

U.S. PATENT DOCUMENTS

| | | | |
|---|---|---|---|
| 4,225,410 | 9/1980 | Pace | 204/403 |
| 4,534,356 | 8/1985 | Papadakis | 128/635 |
| 4,734,184 | 3/1988 | Burleigh et al. | 204/409 |
| 4,743,300 | 5/1988 | Brinduse et al. | 106/38.22 |
| 4,803,239 | 2/1989 | Schaberg | 524/428 |
| 4,871,439 | 10/1989 | Enzer et al. | 204/401 |
| 4,908,112 | 3/1990 | Pace | 204/299 R |
| 4,912,171 | 3/1990 | Grootaert et al. | 525/340 |
| 5,266,650 | 11/1993 | Guerra et al. | 525/326.4 |
| 5,284,568 | 2/1994 | Pace et al. | 204/403 |
| 5,371,143 | 12/1994 | Novak et al. | 525/88 |
| 5,401,376 | 3/1995 | Foos et al. | 204/409 |
| 5,547,555 | 8/1996 | Schwartz et al. | 204/418 |

FOREIGN PATENT DOCUMENTS

| | | |
|---|---|---|
| 0 311 377 | 12/1989 | European Pat. Off. . |
| 0 351 516 | 1/1990 | European Pat. Off. . |

OTHER PUBLICATIONS

Allan T. Worm, "Fluoroelastomers Driving Toward The Future", Machine Design, Jun. 6, 1994, pp. 84–92.

Albert van den Berg et al., "Silicon–Based Chemical Sensors and Chemical Analysis Systems", Sensors and Materials, vol. 6, No. 1, 1994. No month available.

Urs Oesch et al., "Ion–Selective Membrane Electrodes for Clinical Use", Clinical Chemistry, vol. 32, No. 8, pp. 1448–1459, 1986. No month available.

M. Koudelka, "Performance Characteristics of a Planar 'Clark–Type' Oxygen Sensor", Sensors and Actuators, vol. 9, pp. 249–258, 1986. No month available.

Ph. Arquint et al., "Integrated Blood–Gas Sensor for $pO_2$, $pCO_2$ and pH",, Sensors and Actuators B, vols. 13–14, pp. 340–344, 1993. No month available.

S. J. Pace et al., "A Thick Film Multi–Layered Oxygen Sensor", pp. 406–409, 1985. No month available.

Gem® Systems Technical Summary, Mallinckrodt Sensor Systems, Jun., 1989.

Ash, "Handbook of Plastic Compounds, Elastomers, and Resins", pp. 559–563, VCH (1992). No month available.

*Primary Examiner*—Bruce F. Bell
*Attorney, Agent, or Firm*—Arthur S. Morgenstern; Timothy J. Oyer; Robert P. Blackburn

[57] ABSTRACT

An elastomer, especially a fluoropolymeric elastomer, meets requirements necessary for use as a gasket in contact with primary membranes of electrochemical sensors of both blood gas and ionic species in blood. The elastomer can electrochemically seal an electrode of a diced chip (sensor) from a sample chamber, and can electrochemically seal electrodes of neighboring diced chips from each other. Significant simplicity in fabrication of multi-sensor analyzers and stopped-flow method using such analyzers is realized.

75 Claims, 4 Drawing Sheets

FLUOROELASTOMER GASKET FOR BLOOD SENSORS

FIELD OF THE INVENTION

The invention relates generally to electrochemical sensors for determining analytes in blood samples, and more particularly to a fluoroelastomer useful, particularly as a gasket, in sample containers in such sensors.

BACKGROUND OF THE INVENTION

In the clinical setting it is important to monitor certain blood analytes that are highly relevant to normal physiological function and homeostasis, particularly analytes such as $pCO_2$, $pO_2$, tHb, pH, $Na^+$, $K^+$, $Cl^-$, $Ca^{2+}$, glucose, and lactate. Electrochemical sensors have been developed for analysis of these and other analytes. State-of-the-art electrochemical blood sensors generally are quite small and of an essentially planar structure, comprising layers of relatively thin materials fabricated, for example, using thick-film or thin-film techniques. See, for example, U.S. Pat. No. 4,571,292 (Liu et al.); U.S. Pat. No. 4,536,274 (Papadakis et al.); and U.S. Pat. No. 5,401,376 (Foos et al.), all incorporated herein by reference.

Such small, planar sensors typically include one or more electrodes on a substrate, the electrodes being covered by a solid electrolyte which is in turn covered by a membrane such as a semipermeable or ion selective membrane that interacts with the analyte of interest. Such membranes typically are based upon polyvinyl chloride, polytetrafluoroethylene, polyethylene, polypropylene, and the like.

One type of electrochemical sensor operates as follows. A sample suspected of containing an analyte is placed in contact with a semipermeable membrane of the sensor, the analyte diffuses across the membrane, through an electrolyte, and is oxidized or reduced at an electrode, resulting in current flow at that electrode (via the solid electrolyte and a second electrode). Such an arrangement is typical of a sensor of a gas such as oxygen or carbon dioxide. Another type of sensor, typical of measurement of ionic species such as calcium ion, sodium ion, potassium ion, chloride ion, etc., includes an electrode covered optionally by a solid electrolyte and by an ion selective membrane. A fluid sample suspected of containing the analyte contacts the membrane, a second electrode also contacts the fluid sample, and a potential is established between the electrodes. Interaction of the analyte with a corresponding ionophore in the membrane alters the electrical potential across the membrane, which is measured as a change in potential between the two electrodes.

It is a goal in the clinical setting to maximize the amount of data obtainable from a sample having a volume as small as possible, typically a sample on the order of microliters. Accordingly, in planar sensors such as those described above, it is desirable to fabricate a sample container that can receive a fluid sample of very small volume and hold the sample in contact with the primary membrane, the container being made of material that will not adversely affect analyte determination, any adverse effect being magnified as sample volume decreases. Such a container may be defined by a cover and a portion of the primary membrane that faces the cover. The container may include an elastomeric material, such as an elastomeric gasket that forms a seal between an edge of the cover and the semipermeable membrane. Fabrication of a gasket for use in such an arrangement is, however, not trivial. A material suitable for use as a gasket preferably will not adsorb or absorb components from a fluid sample in a way that analyte measurement is affected or the lifetime of the gasket is shortened, nor will a suitable material contain species that leach into a fluid sample and affect analyte measurement or adversely affect the primary membrane thereby shortening the lifetime of the sensor. Similarly, the gasket desirably will not absorb species directly from the primary membrane, nor leach species directly into the membrane.

It is also a goal in the clinical setting to analyze a single fluid sample for a plurality of analytes, simultaneously. Yet, each of the above-described generalized types of electrochemical sensors requires a gasket having unique characteristics. In a typical gas sensor, analyte gas permeability and solubility of the gasket should be low. In sensors that operate by detecting a change in potential between electrodes on opposite sides of a primary membrane containing an ionophore (thereby detecting changes in electrical potential across the membrane), the gasket may be required to electrochemically seal the electrodes from each other, therefore the electrical resistance across the gasket must be high. In each case, the gasket should not interact chemically with the membrane, or the gas permeability or ionic sensitivity of the membrane may be affected. In pH sensors, most of these requirements are present. Thus, the development of gaskets for use in various sensors is complicated.

Electrochemical sensors that measure fluid samples such as blood may be continuous-flow sensors or stopped-flow sensors. In continuous-flow sensors, a fluid sample is allowed to flow adjacent a sensing area of a primary membrane, and an analyte in the sample is determined while the sample flows. In a stopped-flow sensor, a fluid sample is brought into contact with the sensing area of a semipermeable membrane, and an analyte in the sample is determined while the sample is stationary, or prevented from flowing. Stopped-flow sensor arrangements are desirable in many instances, since the volume of sample required for each analysis is minimized. However, materials such as gaskets that form part of sample containers in stopped-flow systems must be carefully developed, since undesirable characteristics of such materials can be amplified as the volume of sample decreases relative to the surface area of a container that holds the sample (and/or decreases relative to the volume of a material that forms in part the container and that absorbs sample components).

U.S. Pat. No. 4,454,007 (Pace); U.S. Pat. No. 4,734,184 (Burleigh et al.); U.S. Pat. No. 4,871,439 (Enzer et al.); U.S. Pat. No. 5,284,568 (Pace et al.); and International Publication No. WO 91/11710 (Joseph et al.) each describe sensor arrays that meet some of the characteristics desirable in electrochemical analysis arrangements. However, the prior art fails to provide disclosure and teachings necessary to fabricate an electrochemical analyzer, or sensor array, that has a container including a gasket that meets many goals of modern electrochemical analysis.

Accordingly, it is a general purpose of the present invention to provide an electrochemical analyzer that is equipped to measure the concentration both of gases, such as carbon dioxide and oxygen, and ionic species in a test sample such as blood, which analyzers are small and efficient to manufacture. It is additionally a general purpose to provide methods for analyzing these species in such sensors using stopped-flow or continuous-flow protocols.

SUMMARY OF THE INVENTION

The foregoing and other objects and advantages of the present invention are achieved by providing an elastomer that has properties desirable for use in an electrochemical analyzer, allowing for several advantageous analyzer arrangements and methods. According to one embodiment, an electrochemical analyzer includes an electrochemical sensor and a sample container adapted to position a sample on a sensing area of the sensor. At least a portion of the container is defined by an elastomeric fluoropolymer. The sensor generally includes a primary membrane that covers one or more electrodes and, optionally, an electrolyte. The elastomeric fluoropolymer is contiguous with the primary membrane according to a preferred embodiment. The analyzer can include one or more sensors, and in multi-sensor embodiments the elastomeric fluoropolymer can be contiguous with primary membranes of two or more sensors. For convenience, a single portion of an elastomeric fluoropolymer can be contiguous with two or more membranes. The analyzer can include a cover adapted to receive a fluid sample, and the elastomeric fluoropolymer can define a gasket between the cover and one or more primary membranes. According to one aspect, the gasket forms an electrochemical seal between a side of the membrane that faces the sample and an electrode in electrical communication with the other side of membrane. As described below, this is particularly advantageous from the perspective of low-cost analyzer fabrication.

The invention also provides an electrochemical analyzer including two or more electrochemical sensors, the first of which is constructed and arranged for determining a gas, and the second of which is constructed and arranged for determining an ionic species. Each sensor of the analyzer includes a container adapted to position a sample at the primary membrane of that sensor. An elastomer forms a part of each container, the elastomer being contiguous, in each case, with the primary membrane of the respective sensor, and the elastomer at each sensor essentially the same. The elastomer can be a fluoropolymer, and a continuous portion of the elastomer may be contiguous with the membranes of both the first and second sensors. The containers of the first and second sensors can be connected (or continuous) such as in a single flow channel, and the elastomer can be a gasket or gaskets that aid in sealing the primary membranes which define in part such a channel. According to one aspect, the elastomer forms an electrochemical seal between an electrode of a sensor on one side of the membrane and components of the system on a side of the membrane opposite of the first side, for example a second electrode such as a second working electrode or a reference electrode. According to another aspect the elastomer forms an electrochemical seal between electrodes of two or more sensors in an analyzer.

The invention also provides methods for determining analytes in fluid samples such as blood. According to one embodiment, a method involves delivering a fluid sample suspected of containing an analyte into an electrochemical analyzer sample container, the container including a primary membrane of a first sensor constructed and arranged for determining a first analyte, a primary membrane of a second sensor constructed and arranged for determining a second analyte, and an elastomer that is contiguous with the primary membrane of the first sensor. The method involves preventing the sample from flowing, and determining at least the first analyte while the sample is stationary, preferably the first and second analytes simultaneously. The elastomer can be a fluoropolymer, and a continuous portion of the elastomer can be contiguous with the primary membrane of each sensor. The method can involve simultaneous determination of a gas and an ionic species at individual sensors, in which each sensor includes an electrochemical seal, formed by the elastomer, between an electrode and a surface of a primary membrane opposite the electrode. The methods of the invention can be practiced with any suitable devices described.

The invention also provides an electrochemical analyzer including an electrochemical sensor that has a heterogenous membrane with a surface, a portion of the surface adapted for receiving a sample for electrochemical analysis. The analyzer includes a sample container adapted to position a sample at the sensing area. A portion of the sample container is formed of an essentially gas-impermeable elastomer that is contiguous with the heterogeneous membrane.

Other features and advantages of the invention will be apparent from the description of the preferred embodiments thereof, and from the claims.

BRIEF DESCRIPTION OF THE DRAWINGS

The above and other features, objects and advantages of the present invention will be better understood from the following specification when read in conjunction with the accompanying drawings, in which.

DETAILED DESCRIPTION OF PREFERRED EMBODIMENTS

The present invention provides electrochemical analyzers and methods of electrochemical analysis that incorporate, as a portion of a container that holds a sample in contact with a sensing surface of an analyzer, an elastomer having certain advantageous properties. The invention allows for heretofore unavailable combinations of sensors, each specific for a particular analyte, in a single analyzer fabricated using highly efficient procedures. The invention also allows for heretofore-unavailable methods of stopped-flow electrochemical analysis simultaneously of certain analytes using an analyzer manufactured highly efficiently.

Figure 1:
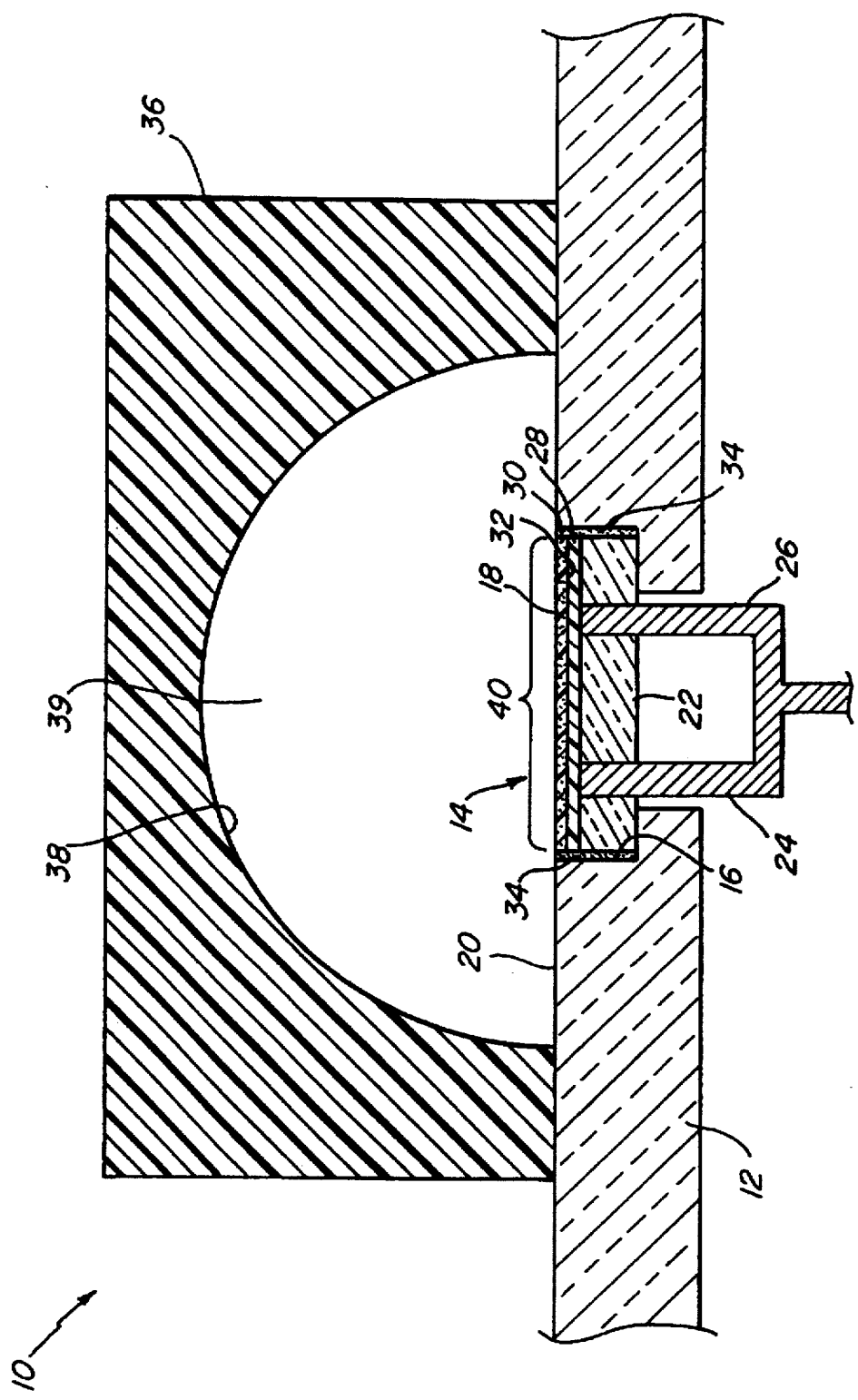
FIG. 1 is a schematic, cross-sectional view of a single-sensor electrochemical analyzer according to one embodiment of the invention.

FIG. 1 illustrates schematically, in cross-section, an electrochemical analyzer 10 according to one embodiment of the invention. The arrangement of components as shown in FIG. 1 is known. However, the prior art does not describe a fluoroelastomer as component 36 of FIG. 1 or as any portion that in part defines container 39. Analyzer 10 includes a substantially planar base, or substrate 12, and a planar-type sensor 14 in an indentation 16 of base 12 that is shaped to receive sensor 14 such that an essentially planar sensing surface 18 of the sensor is approximately flush with a surface 20 of the base. Sensor 14 includes a substrate 22 through which a first electrode 24 and a second electrode 26 pass. As illustrated in this and subsequent figures, electrodes 24 and 26 are electrically crossed, or shorted, such that an essentially one-electrode sensor is defined. Sensors having any number of electrodes can include the elastomer of the invention, for example one-electrode sensors typical of ion sensors, two-electrode sensors as described in U.S. Pat. No.

4,536,274, referenced above, three-electrode sensors as described in U.S. Pat. No. 5,401,376, referenced above, and sensors having additional electrodes. An array of sensor chips can be fabricated with any particular number of electrodes. Some of the electrodes may be crossed, as illustrated in the figures, to effectively reduce the number of electrodes if desired. In this way, a single type of chip can be adapted to serve as one of several types of sensors.

An electrolyte layer 28 coats a side of substrate 22 that faces the sensing surface 18 of the sensor, and contacts electrodes 24 and 26, and a primary membrane 30 coats electrolyte 28. As used herein, the term "primary membrane" is meant to define any of a wide variety of membranes suitable for use in a sensor to separate a sample from an electrode, and which is adapted to facilitate determination of an analyte. For example, a membrane that contains a species (such as an ionophore) that is affected by an analyte such as an ion in such a way that measurement of the analyte can be carried out, or through which an analyte (such as a gas) can pass from the sample to an electrode for determination. As illustrations, membranes that are semipermeable to a gas such as oxygen are contemplated, as well as heterogeneous membranes such as solvent polymeric membranes or liquid membranes (discussed below).

The primary membrane includes a first surface 32 that contacts electrolyte 28, and that is thus in electrical communication with electrodes 24 and 26, and a second surface 18 opposite surface 32 that is the sensing surface.

Sensor 14 illustrates schematically a type of planar, solid-state sensor that is very cost-efficient to manufacture. A process for manufacturing such a sensor can involve fabricating many sensors on a single wafer (in which a single membrane layer on a single electrolyte layer is cast, for example), and dicing the wafer to define many individual sensors. As a result, each sensor includes peripheral edges that expose the various layers from which the sensor is fabricated. In the sensor illustrated, electrolyte 28 is exposed at the edges of the sensor. Accordingly, an adhesive 34, such as an epoxy or cyanoacrylate adhesive, can be introduced into spaces between the edge of sensor 14 and the border of indentation 16 within which sensor 14 resides. Adhesive 34 is designed to prevent components of a fluid sample from interfering with the function of electrolyte 28 and to prevent leaking from the sample container, described below.

Analyzer 10 includes a cover 36 that, according to the embodiment illustrated, is a single-piece unit including a semispherical cavity having an interior surface 38. Cover 36, when placed upon base 12, completes a sample container 39.

The semispherical cavity of cover 36 that defines in part container 39 has a diameter greater than the largest dimension of sensing surface 18, and is centered above sensing surface 18, thus all of sensing surface 18 defines a sensing area 40 of sensor 14 according to the embodiment illustrated.

According to the embodiment of the invention illustrated, cover 36 is an elastomer having certain advantageous properties. Elastomeric material suitable for use in connection with the invention is advantageously formulated from a material which, when it defines an entire cover, a portion of a cover, or is held firmly between a cover and primary membrane to form in part a sample container (described below with reference to FIG. 3) does not compromise sensor performance (use) or shelf life as compared to a similar sensor that does not include elastomeric material. In particular the elastomeric material of the invention can be used in a sensor and provides the sensor with a shelf life of at least 30 days, preferably 60 days, more preferably six months, and according to a particularly preferred embodiment at least twelve months.

Typically, the elastomer is formulated from a durable organic polymer which does not creep or flow when stressed, which has a low durometer rating, providing a good seal such as a hermetic seal (in embodiments described below, for example), which is gas impermeable, and which may be slightly hygroscopic and thus may swell slightly in the presence of solution containing water, which in some instances will aid sealing at a membrane.

Preferably, the elastomer has a hardness of less than about 100 on the Shore A scale, more preferably a hardness of from about 50 to about 90 on the Shore A scale, and most preferably a hardness of from about 65 to about 75 on the Shore A scale.

The elastomer desirably has sub-microscopic properties which make it gas impermeable, and is thus preferably formulated from a precursor having a sufficient degree of unsaturated carbon-carbon bonds to form a sufficiently highly cross-linked polymer compound when cured, or have other means of attaining such a degree of cross-linking. Specifically, the elastomer that defines cover 36 has low carbon dioxide and oxygen permeability. In particular, its permeability to carbon dioxide is desirably less than about 100 barrers, more preferably less than about 40 barrers, and most preferably less than about 20 barrers. Its permeability to oxygen is desirably less than about 20 barrers, preferably less than about 10 barrers, and more preferably less than about 5 barrers. A Barrer is a unit of gas permeability defined by amount permeant (at standard temperature and pressure) multiplied by the thickness of the material, and divided by the area of the material, the pressure differential across the material in that area, and unit time. The Barrer is defined by Equation 1.

$$1 \text{ Barrer} = 10^{-10} \times \frac{\text{permeant (cm}^3\text{)} \times \text{thickness (cm)}}{\text{area (cm}^2\text{)} \times \text{time (s)} \times P_{dif} \text{ (cm Hg)}} \quad \text{(Eq. 1)}$$

Permeability values in Barrer units may be obtained according to the following method. Material to be tested is mounted so as to be contacted on a first side by flowing water having a partial pressure of oxygen equal to the partial pressure of oxygen in air, and contacted on a second side opposite the first side with flowing carrier gas such as nitrogen. The areas on the first and second sides of the material contacted by water and carrier gas, respectively, are of equal dimension. The carrier gas flowing past the material is analyzed for oxygen content using a sensor such as a potentiometric palladium oxygen sensor. Using measured values of permeant as a function of time, the area of the material contacted by water on the first side and by carrier gas on the second, the thickness of the material, and the oxygen partial pressure differential across the material, permeability values in Barrer units according to Equation 1 are determined.

The solubility of carbon dioxide in the elastomer is desirably less than about 200 $cm^3$(at STP)/$cm^3$·atm, preferably less than about 125, more preferably less than about 75 $cm^3$(at STP)/$cm^3$·atm. The solubility of oxygen in the elastomer is desirably less than about 50, preferably less than about 30, and more preferably less than about 20 $cm^3$(at STP)/$cm^3$·atm.

According to embodiments in which the elastomer is an organic polymer, it is fabricated so as not to contain a substantial amount of mobile extractable materials such as plasticizers that could leach into a sensor primary membrane directly, or via a fluid sample. Such leaching of extractables can affect the microscopic physical properties of the membrane, disadvantageously effecting a change in its permeability characteristics or ionic or electrical properties. This is an especially notable consideration with respect to sensors designed for long-term use, on the order of, for example, days or months, and with respect to sensors operating with small test sample volumes. Additionally, the elastomer should be free of any species which could migrate into a fluid sample contacting the elastomer, affecting electrochemical measurements, and/or destroying sensor components. Material used in the formation of elastomer is preferably selected to be essentially free of mobile transition and main group metals, especially battery metals such as iron, cobalt, nickel, lead, copper, extractables, and species such as sulfides which are deleterious to preferred electrode materials, such that electrochemical response is not affected over long-term sensor use, specifically for at least 2 days of normal sensor operation.

The elastomer should be resistant to plasticizer uptake. In particular it should have less than about 10% by weight plasticizer uptake, preferably less than about 5% by weight plasticizer uptake, more preferably less than about 1% by weight plasticizer uptake. The elastomer should be essentially free of mobile extractables such as sulfur and hydrocarbon. The elastomer also should be essentially free of mobile heavy metals and alkali or alkali earth elements such as calcium, magnesium, sodium, cesium, lithium, and potassium. Oxides such as calcium oxide and zinc oxide are not particularly disadvantageous, but should be present in low concentration, if present at all, and a material containing such oxides should be tested to determine whether the oxides impart disadvantageous results.

A simple test to screen materials that are candidates for use as the elastomer of the invention is to expose a candidate material to a particular solvent, determine the change in weight of the material before and after exposure and drying, and thereby determine the amount of material that has leached out of or into the material. For example, materials can be exposed to tetrahydrofuran for several hours, dried, and weighed. A significant loss in weight, for example a loss in weight of at least 10%, is an indication that the candidate material may contain leachables that could be detrimental for use in accordance with the invention. According to another test, a candidate material is exposed to diundecyl phthalate and dried. In this case, a gain in weight of the material of greater than about 5% may indicate that the material, if placed in a sensor at a position contiguous with a membrane, may absorb species such as plasticizers from the membrane (particularly a heterogeneous membrane such as a solvent polymeric membrane or liquid membrane), detrimentally affecting the performance of the membrane.

The elastomer of the invention should have a high electrical resistance. The structure formed by the material should provide wet resistance of at least 50 gigaohms and preferably at least 100 gigaohms between regions desirably electrically isolated from each other. The term "wet resistance" is meant to define resistance when the sensor is exposed to a fluid sample such as blood, a reference solution, or fluid such as saline introduced into the sensor for storage, and has been exposed to the fluid for a period of time equal to typical start-up and stabilization time.

Heterogeneous membranes are especially damaging, in general, to adjacent elastomers. A heterogeneous membrane, such as a solvent polymeric membrane or liquid membrane, is a membrane containing a mobile carrier in an inert matrix such as plasticized PVC. Such mobile carriers can include charged carriers such as ion-exchangers, or neutral carriers such as ionophores. Performance of these heterogeneous membranes is especially compromised with heretofore-known elastomers that are contiguous with such membranes, and prior art sensors have not been fabricated using heterogeneous membranes contiguous with elastomers that have gas permeability low enough for determining a gas or a species whose concentration is dependant on a gas. In particular, pH sensors for use with samples that contain carbon dioxide, such as blood samples, are particularly difficult to use in conjunction with an elastomer contacting the sensor membrane since the concentration of the hydrogen ion, which is affected by $CO_2$ concentration, is measured. Accordingly, another embodiment of the invention involves an electrochemical sensor having a heterogeneous membrane such as a solvent polymeric membrane or liquid membrane and an elastomer contiguous with the membrane. Preferably, the elastomer has a permeability to oxygen or carbon dioxide as described above with respect to the elastomer that defines cover 36.

The elastomer material is typically formed from a highly cross-linked elastomeric compound. Any elastomeric material which meets all the purity and physical requirements listed above may serve. A preferred embodiment of this material is a fluoropolymer-based elastomer that optionally contains one or more of additives, for example calcium hydroxide, magnesium oxide, titanium dioxide, and the like, that contribute to certain desirable characteristics in the elastomer. Suitable fluoroelastomers are described in U.S. Pat. No. 4,743,300 (Brinduse et al.); U.S. Pat. No. 4,803,239 (Schaberg); U.S. Pat. No. 4,912,171 (Grootaart et al.); U.S. Pat. No. 5,266,650 (Guerra et al.); and U.S. Pat. No. 5,371,143 (Novak et al.) all incorporated herein by reference. Suitable fluoroelastomers are available from Ausimont (Morristown, N.J.) sold under the trademark Tecnoflon; from DuPont (Wilmington, Del.) sold under the mark Kalrez and the mark Viton; from the Minnesota Mining and Manufacturing Co. (3M), in particular a copolymer of chlorotrifluoroethylene and vinylidene fluoride sold under the mark Kel-F; and from Ethyl (Baton Rouge, La.), perfluoroalkoxyphosphazene, sold under the mark Eypel F. According to a preferred embodiment, a copolymer of vinylidene fluoride and hexafluoropropylene forms the basis of the elastomer, and a particularly preferred elastomeric material is a product sold as KM-2-41-2 by Cri-Tech, Inc., Hanover, Mass. which is a composition including about 71% by weight of a vinylidene fluoride-hexafluoropropylene copolymer sold under the trademark Fluorel by the Minnesota Mining and Manufacturing Co., containing about 3.2% by weight calcium hydroxide, about 3.2% by weight magnesium oxide, and about 21.2% by weight titanium dioxide.

Any of a variety of methods for forming the elastomer of the invention into a gasket, cover, or portions of a cover (these components described with reference to the figures) can be carried out, such as injection molding, compression molding, solvent casting, and the like. Curing the material via heat, UV radiation, etc. can follow. In some instances, it is desirable to carry out formulation and formation of the gasket in a sulfur-free environment.

The fluoroelastomer used can be in a variety of forms and shapes all of which act as gas sealants for the container. For example, in most cases, the fluoroelastomer used is either the entire material of the container or more preferably a conventional encircling gasket having an internal space for the sensing membrane surface and an encircling gasket portion acting to seal an edge of the membrane. In some cases, the fluoroelastomer material can be in the form of a plug to close the container after it is formed. Any use of a fluoroelastomer to seal the container is referred to as a "gasket" in this invention. Conventional gasket forms such as flat, sheet, cut, o-ring and other cross-sectional shapes can be used. The gaskets are preferably used in continuous encircling forms as, for example, o-rings.

As illustrated and described (for purposes of simplicity), cover 36 is made of a single material, that is, an elastomer having particular advantageous properties according to the invention. Cover 36 can be formed, however, of a variety of materials, only one of which is an elastomer of the invention. For example, the bulk of cover 36 could comprise a relatively rigid structure, such as inert plastic or ceramic, with portions of the cover that contact base 12 being elastomeric. Additionally, the cover 36 can be of any of a variety of desirable shapes or dimensions other than the shape and dimension illustrated. For example, cover 36 can be fabricated to include an interior surface 38 having topography that is advantageous in a continuous-flow sensor, or can be shaped to minimize the volume of sample container 39 in a stopped-flow arrangement where desired.

Figure 2:
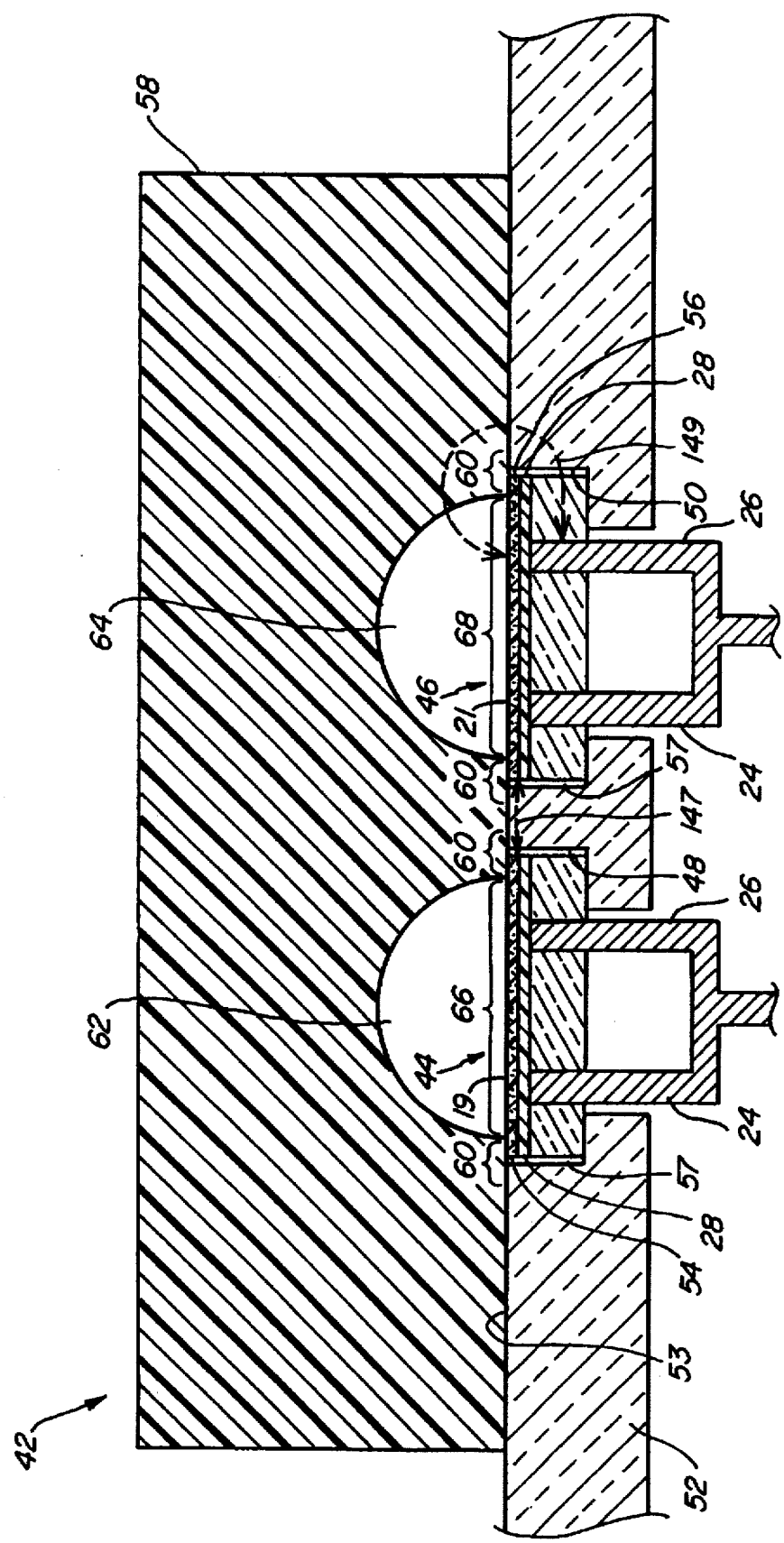
FIG. 2 is a schematic, cross-sectional view of a multi-sensor electrochemical analyzer according to one embodiment of the invention.

Referring now to FIG. 2, a multi-sensor analyzer 42 is illustrated schematically in cross-section. In all of the figures, some components that are similar to various figures are represented by a single number. Analyzer 42 includes a first sensor 44 and a second sensor 46 in indentations 48 and 50, respectively, of a base 52. In the analyzer illustrated in FIG. 2, and all analyzers described herein, the sensors, base, cover member, and other components can be replaced with similarly-functioning components. For purposes of simplicity sensors 44 and 46 are illustrated as identical to sensor 14 in FIG. 1. It is to be understood, however, that the invention resides in a particularly useful elastomer in association with an electrochemical analyzer, and methods that are enhanced via use of such an elastomer, and that sensors can be of a variety of types.

According to one embodiment of the invention, a multi-sensor analyzer includes a sensor 44 for determining a gas and a sensor 46 for determining an ionic species. As used herein, the term "gas sensor" includes sensors of pH in a sample containing carbon dioxide. As used herein, the terms "determine", "determining", "determination", "analyze", "analyzer", and "analysis", in the context of an analyte, means electrochemically sensing the presence of and/or concentration of a particular analyte in a medium brought into contact with a sensing area of a sensor, via exploitation of known electrochemical principles.

A gas sensor 44 will include a primary membrane 54 that is a semipermeable membrane that has the requisite gas permeability properties and electrochemical properties, such as a membrane as described in U.S. Pat. No. 5,401,376, referenced above. A sensor 46 specific for an ionic species will include a primary membrane 56 such as a heterogeneous membrane, typically including an ionophore, which facilitates determination of a predetermined ion. Such membranes and ionophores are known to those of ordinary skill in the art, as described in International Publication No. WO 91/11710, referenced above.

As illustrated, analyzer 42 includes a cover 58 that has formed therein two semispherical cavities, each centered above a sensor 44 or 46. According to one embodiment, cover 58 is made of the elastomer of the invention. Unlike the semispherical cavity illustrated in FIG. 1, the cavities of FIG. 2 are smaller in diameter than the smallest dimension across sensing surface 19 or 21 of each of primary membranes 54 and 56, respectively, thus sample containers 62 and 64 defined in part by these cavities each include a portion of sensing surface 19 or 21 of a primary membrane, the portions defined as sensing areas 66 and 68, and an interior surface of a semispherical indentation in cover 58, but do not include a portion of surface 53 of base 52. In the embodiment illustrated, each of the boundaries between surface 53 of base 52 and sensing surface 19 or 21 of a sensor is bridged by the elastomer of the invention.

FIG. 2 illustrates an arrangement that is particularly convenient and efficient to manufacture. In particular, first and second sensors 44 and 46 can each be manufactured, in bulk, from a diced wafer of like sensors. However, according to the embodiment illustrated, adhesive need not be applied in gaps 57 between the edges of sensors 44 and 46 and the perimeters of indentations 48 and 50 within which sensors 44 and 46 reside, respectively. While the lack of adhesive filler means that electrolyte 28 is exposed at the edge of each of sensors 44 and 46, electrodes 24 and 26 are electrochemically sealed from sensing areas 66 and 68 of the sensors by regions 60 of cover 58 that each bridge surface 53 of base 52 and sensing surface 19 or 21 of one of primary membranes 54 or 56. This is particularly important in arrangements in which the sensor operates by measuring a potential difference between an electrode 24 or 26 and a reference electrode (not shown) that contacts a sample which is also in contact with one of the sensing areas 66 or 68. As used herein, the term "electrochemical seal" is meant to define a seal that, when the sensor is exposed to a medium such as a fluid medium carrying an analyte to be determined at a sensing surface of a membrane, provides electrical resistance between an electrode within the sensor and the sensing surface of the membrane (the surface opposite the surface that is intended to be in electrical communication with the electrode), via a pathway 149 (as illustrated in connection with sensor 46) that circumvents the primary membrane, that is at least twice, preferably about five times, and more preferably about ten times the electrical resistance across the primary membrane.

As mentioned, cover 58 can be made entirely of the elastomer of the invention. Alternatively, cover 58 can be made of more rigid plastic or ceramic, with regions 60 of cover 58 that each bridge surface 53 of base 52 and sensing surface 19 or 21 of one of primary membranes 54 or 56, being made of the elastomer of the invention. Alternatively, cover 58 can include elastomeric portions anywhere so long as the elastomeric portions seal sensing areas 66 and 68 electrochemically from electrodes 24 and/or 26. For example, an arrangement can include a cover 58 that is relatively rigid, with a gasket that is made of the elastomer of the invention placed between cover 58 and portions of sensing surfaces in register therewith so as to define an isolated sensing area 66 or 68 on primary membranes 54 or 56 adapted to receive a sample. That is, a sensing area can be created that is of any area less than or equal to the area of the sensing surface of a primary membrane with use of the elastomer of the invention, and additional sealing of the edges of the sensors (additional isolation of the sensor electrodes or electrolyte from the sample area), for example with adhesive, is not required.

The term "electrochemical seal" is defined above, and a further definition of this term in accordance with the invention, with reference to FIG. 2, includes a seal formed between electrodes, or electrolyte 28 of adjacent sensors 44 and 46. That is, where a sensor electrode or electrolyte (or other component that is in electrical communication with an sensor electrode) is not electrically insulated from a like component of a sensor in the same analyzer, the elastomer of the invention can electrochemically seal the components of the neighboring sensors from each other. Where the elastomer of the invention bridges a sensing surface 19 or 21 of a sensor and an adjacent surface 53 of a base 52, and an adjacent sensor also includes a sensing surface 19 or 21 and adjacent surface 53 of base 52 that is bridged by an elastomer, a pathway 147 between electrolyte 28 of adjacent sensors (or between electrodes of adjacent sensors) has a resistance at least twice, preferably five times, and more preferably at least ten times as great as the resistance across one of the primary membranes of the analyzer. According to this embodiment, the wet resistance between electrodes of adjacent sensors is at least 50 gigaohms, preferably at least 100 gigaohms.

Sensors 44 and 46 can be constructed and arranged to determine a single analyte, or different analytes. According to one embodiment, sensor 44 is constructed and arranged for determining a gas such as carbon dioxide or oxygen (or gas-dependant species such as pH in the presence of the gas to which it is sensitive), and sensor 46 is constructed and arranged for determining an ionic species such as sodium ion, potassium ion, chloride ion, or calcium ion. The elastomer of the invention allows for the manufacture of an analyzer that contains such sensors together, preferably addressed by a single sample container, in which the electrodes of the sensors are electrochemically sealed from each other solely by the elastomer. The electrochemical seal is adequate to allow stopped-flow analysis in such an analyzer. For example, sample container 62 and sample container 64 can be interconnected, thus defining in essence a single container. A stopped-flow analyzer can include an injector adapted to inject a metered dose of fluid sample in an amount essentially equal to the volume of the container that is a combination of container 62 and 64, or a slightly larger volume if required for stopped-flow analysis by the analyzer. This will minimize the volume of sample consumed. The analyzer also can include a mechanism constructed and arranged to determine both the gas analyte at sensor 44 and the ionic species analyte at sensor 46 while a sample is positioned at sensing areas 66 and 68 and is prevented from flowing. Such a mechanism can include a sensor that is triggered by the injection of a fluid sample into the containers and the completion of such injection, and automatically carries out electrochemical measurements that determine the gaseous analyte at sensor 44 and the ionic species analyte at sensor 46. These mechanisms are known.

Figure 3:
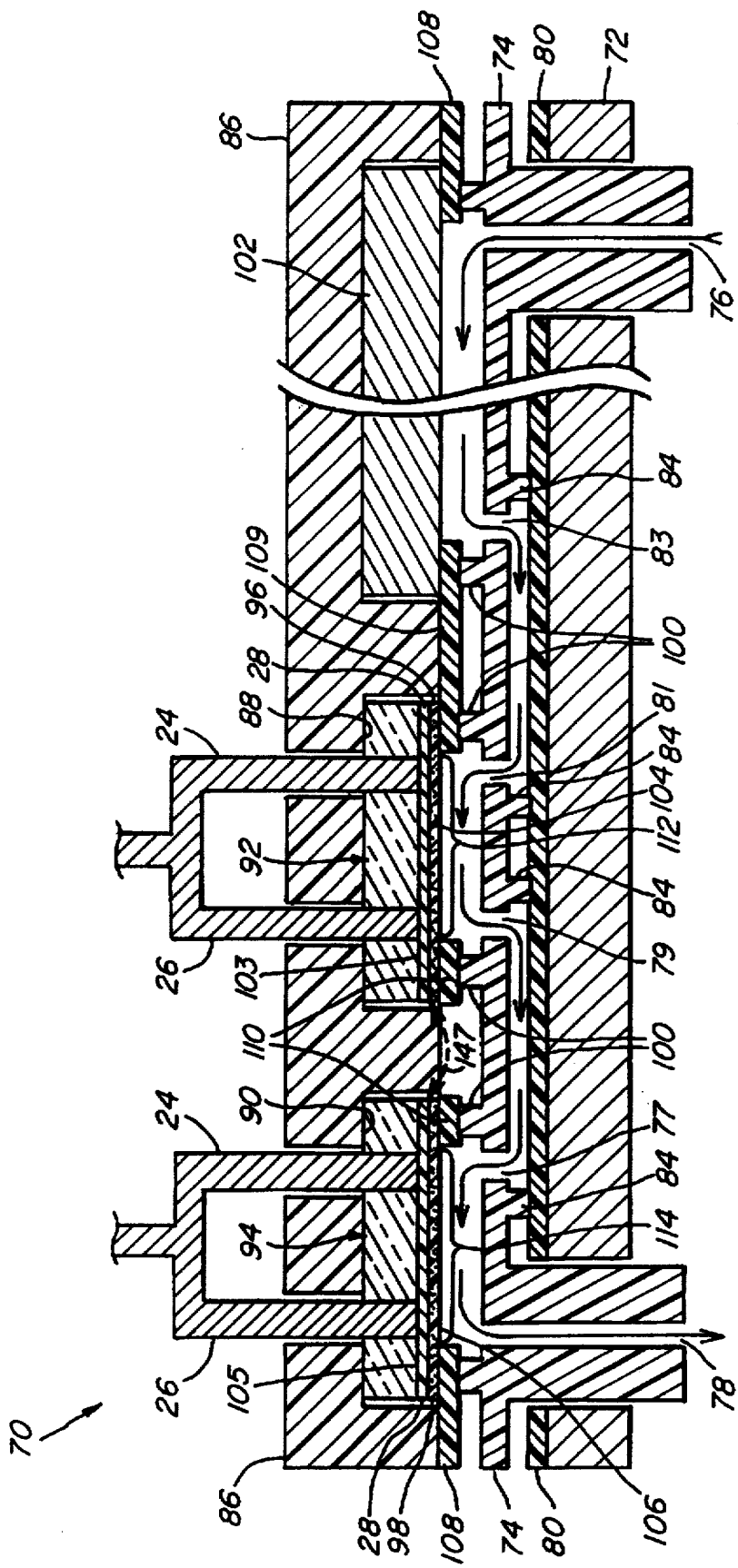
FIG. 3 is a schematic, cross-sectional view of a multi-sensor electrochemical analyzer according to another embodiment of the invention.

In FIGS. 1 and 2 above, the elastomer of the invention comprises an entire cover that defines a container for providing a sample in contact with a sensing area of a sensor, or comprises any portion of such a cover, and according to a preferred embodiment comprises a gasket between a somewhat rigid and inert cover and a base or, according to a particularly preferred embodiment, a primary membrane of a sensor. Referring now to FIG. 3, an electrochemical analyzer 70 is illustrated schematically in cross section which can include any number of sensors, can provide for continuous-flow or stopped-flow analysis, and can be manufactured very efficiently using sensors made from diced wafers of a plurality of like sensors, electrochemically sealed using solely the elastomer as gasket material. Analyzer 70 includes a metal heater plate 72 for maintaining constant and stable temperature of a fluid sample to be analyzed. A flow cell 74 constructed of inert plastic or ceramic includes a sample inlet 76 at a first end in fluid communication with a sample outlet 78 at a second end. The flow cell includes a substantially planar portion between the sample inlet and outlet, and a series of holes 77, 79, 81, and 83 through the planar portion through which fluid sample can flow from one side of the essentially planar flow cell to the other. A crossover gasket 80 resides between heater plate 72 and flow cell 74, the flow cell spaced from the crossover gasket by way of a plurality of downwardly-depending protrusions 84 on the flow cell. Downwardly-depending protrusions 84 form fluid seals at crossover gasket 80 such that fluid sample can reside between flow cell 74 and crossover gasket 80 and between adjacent protrusions 84 without leaking. An optional fluid sealer made of electrically insulative material can be placed between crossover gasket 80 and heater plate 72 so that, in the event of any leakage, no electrical shortage can occur via heater plate 72. Crossover gasket 80 can be made of the elastomer of the invention, or any material or combination of materials that does not adversely affect a fluid sample and that provides for fluid seals at protrusions 84.

Above flow cell 74 and in register therewith is a base 86 that, similar to bases 12 and 52 of FIGS. 1 and 2, respectively, includes indentations 88 and 90 that carry sensors 92 and 94, respectively, and an optional preheater chip 102. Sensors 92 and 94, like sensors described above, include electrodes 24 and 26, electrolyte 28, and primary membranes 96 and 98, respectively. Primary membranes 96 and 98 have respective surfaces 103 and 105 that are in electrical communication with sensor electrodes, and opposing sensing surfaces 104 and 106. Sensor 92, according to a preferred embodiment, is adapted to determine a gas such as carbon dioxide or oxygen (or pH in a sample containing $CO_2$), and sensor 94 is adapted for determining an ionic species, as described above, although any combination of sensors can be used.

A sensor gasket 108, comprising the elastomer of the invention, is positioned between flow cell 74 and base 86, and is urged upwardly by upwardly-depending protrusions 100 of flow cell 74 against sensing surface 104 of sensor 92 and sensing surface 106 of sensor 94, defining sensing areas 112 and 114, respectively, of sensing surfaces 104 and 106. Sensor gasket 108 forms, in each sensor, an electrochemical seal between a sensor electrode of each sensor and a fluid sample contacting the sensing area of each sensor, and between electrodes (electrolytes) of adjacent sensors. A gasket, or a plurality of gaskets, can be positioned only where needed to provide seals at primary membranes as illustrated in connection with gasket portions 110 at edges of sensors 92 and 94 or, according to another embodiment that can be easier to manufacture, a gasket including a continuous portion (such as 109) can contact primary membranes of adjacent sensors. This can be envisioned if preheater chip 102 were replaced with a sensor (any number of sensors for determination of any number of a variety of analytes can be provided in analyzer 70). Sensor gasket 108 seals the entire perimeter of each of sensors 92 and 94 at primary membranes 96 and 98, respectively.

Of course, as FIG. 3 is in cross-section, all portions of sensor gasket 108 can be interconnected, as a single continuous portion, or can be individually fabricated as individual gasket portions. "Continuous portion" in this context means a single piece of elastomeric material, containing whatever holes or cut-outs are necessary to provide sealing at desired locations. According to a preferred embodiment, a single, continuous gasket is provided for purposes of simplicity.

Flow cell 74 includes a plurality of upwardly-depending protrusions 100 that maintain the sensors and base in spaced relation from the planar section of the flow cell. Accordingly, regions between protrusions 100, the flow cell planar section, and the sensors or base 86 can contain fluid. Thus, as illustrated, a liquid sample can enter analyzer 70 through sample inlet 76, pass into a region above the planar section of flow cell 74 defined by the flow cell, upwardly-depending protrusion 100, a preheater chip 102 that allows the sample to reach a stable temperature, and sensor gasket, can pass downwardly through a hole 83 in the flow cell into a section below the planar section of the cell defined by the flow cell, downwardly-depending protrusions 84, and crossover gasket 80, can pass upwardly through a hole 81 in the flow cell into a section defined by the planar section of the cell, upwardly-depending protrusions 100, sensing surface 104 of sensor 92, and sensor gasket 108, pass downwardly through a hole 79 into a region defined by the flow cell, downwardly-depending protrusions 84, and crossover gasket 80, and finally pass upwardly through a hole 77 into a region defined by the flow cell, upwardly-depending protrusion 100, sensing surface 106 of sensor 94, and sensor gasket 108.

The word "container", as used herein, is meant to define portions of an analyzer that hold a sample in contact with a sensing area of a sensor membrane. For example, with reference to FIG. 1, the container is defined by the interior surface 38 of cover 36, portions of surface 20 of base 12 that are not covered by cover 36, sensing surface 18 of primary membrane 30, and portions of adhesive 34 that are exposed to the sample. With reference to FIG. 2, sample container 62 includes the interior surface of cover 58 at sensor 44, and sensing area 66 of sensing surface 19 of primary membrane 54. Referring to FIG. 3, the sample container includes all portions that border the flow path illustrated between inlet 76 and outlet 78, including flow cell 74, protrusions 84 and 100, preheater chip 102, sensor gasket 108, crossover gasket 80, and sensing surfaces 112 and 114 of sensors 92 and 94, respectively.

Described above are electrochemical analyzers that can include both diced (exposing electrolyte at edges thereof) gas sensors and diced ionic species sensors in a single array, the sensors sealed electrochemically with a single elastomeric material. As discussed, this facilitates methods involving stopped-flow determination of both a gas and an ionic species with a highly-efficiently manufactured analyzer.

Figure 4:
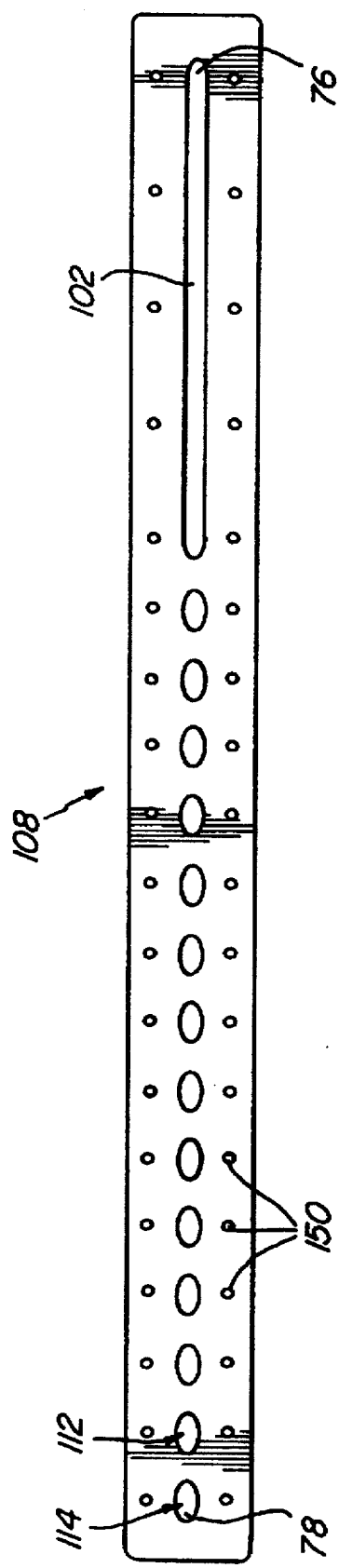
FIG. 4 is a top view of a sensor gasket fabricated from the elastomer of the invention in a geometry for use in the sensor illustrated in FIG. 3.

Referring now to FIG. 4, a top view of sensor gasket 108, fabricated to fit the analyzer of FIG. 3, is illustrated. The gasket includes several cut-outs, and reference numerals refer to components of the analyzer of FIG. 3 that align with certain of these cut-outs. For example, sample inlet 76 is illustrated at the right of the gasket, leading into a pathway that provides for sample flow against preheater chip 102. Sensing areas 112 and 114 of sensors 92 and 94, respectively, are defined by oval cut-outs of sensor gasket 108, as illustrated. Sample outlet 78 is aligned with an edge of sensing area 114. Referring again to FIG. 3, upwardly-depending protrusions 100, shown in cross section, represent portions of oval protrusions sized to isolate sensing areas 112 and 114 of sensors 92 and 94 by compressing the perimeters of the oval cut-outs illustrated in FIG. 4 against the sensing surfaces 104 and 106 of sensors 92 and 94. Cut-outs 150 surround guide protrusions (not shown in FIG. 3) that position the gasket appropriately.

Sensors illustrated in connection with the present invention all are similar in construction to sensor 14. However, while such solid-state, planar-type electrochemical sensors are illustrated, those of ordinary skill in the art recognize that any of a variety of electrochemical sensors that are adapted for determining one or more analytes in a sample can be used in accordance with the invention. These include, without limitation, amperometric or voltammetric, one-electrode or multi-electrode sensors that can include solid, liquid or gel electrolytes. Electrodes, electrolytes, membranes, and other components of sensors that are suitable for use in connection with the invention are described in the above-referenced documents.

The following examples are intended to illustrate the benefits of the present invention, but do not exemplify the full scope of the invention. For example, any thick-film or thin-film technique in planar sensor fabrication can be utilized. Voltammetric and amperometric sensors including any number of electrodes can be utilized. Additionally, sensors that are constructed and arranged to determine the particular gases or ionic species listed herein can be expanded to determination of other analytes. The particular analyte determined is not per se important in the context of the present invention, but it is the different primary membranes that are required for determination of the different types of analytes that, in a single analyzer, present the challenge that is met by the present invention. These and other modifications and their equivalents are understood to be within the scope of the present invention.

EXAMPLE 1

Gasket Fabrication

A fluoroelastomer sheet approximately 0.015 inches thick was formed, and cut into a desired shape for use as a sensor gasket, as follows. Bulk slabs of fluoroelastomer sold by Cri-Tech, Inc., Hanover, Mass, as KM2-41-2 were formed in a thermoset mold into sheets approximately 0.015 inches thick, approximately 1 inches wide, and approximately 5 inches long.

Molding was carried out at 180° C., 7500 psi, for 11 minutes. The material was post-cured at 232° C. for 16 hours. Using water-jet cutting technology, gaskets of the geometry of FIG. 4 were cut (of course, gaskets of any geometry can be formed by this or by more conventional methods such as molding).

EXAMPLE 2 pH Sensor Fabrication

Planar pH sensors were fabricated as follows. A plurality of ion-selective sensors were fabricated by screen printing a plurality of individual electrodes on a laser-scored ceramic wafer, and following the deposition of an ion-selective membrane, the wafer was singulated on the laser score lines so as to create a plurality of individual sensor chips. For the purpose of simplicity in this example, procedures will be described as if a single chip were fabricated.

EXAMPLE 3

Analyzer Fabrication

A sensor was fabricated a follows: An ion-selective sensor base chip was fabricated on a 0.180 cm×0.180 inch electrically insulating alumina composite substrate, available from Coors Ceramic Company, Grand Junction, Colo. The laser score process needed for wafer singulation is available from Lasereliance Technologies, Altamonte Springs, Fla. Holes were laser drilled through the ceramic substrate and filled with electrically conductive metallic paste (gold). Using the thick-film deposition technique, a conductive strip was fabricated on the contact side of the chip (gold) by screen printing to be in electrical contact with the metal conductor in the laser drilled hole. Suitable conductive pastes are available from Metech Company of Elverson, Pa. Another conductive strip (silver) was fabricated on the opposite side (electrode side) of the ceramic to be in electrical contact with the metal conductor in the hole. The conductive strip was fabricated so as to create an oval electrode with the approximate dimensions of 1.52 mm×0.762 mm. Metal pastes were cured per manufacturer's recommendations. In this fashion, electrodes were formed through the substrate, so as to achieve back-side contact. However, as discussed above, any sensor arrangement including front-side electrode contact, can be employed. A dielectric (glass) passivation then was printed over the conductor on the electrode side with an opening so as to define an active electrode area.

In an array of 100 like sensors, the silver electrodes then were galvanostatically plated with silver chloride from 0.1 m KCl for 10 minutes at −5.00 mA. The chip was rinsed in deionized water and air dried.

An electrolyte was formed as follows, a 1% aqueous solution of gelatin was prepared. A buffer including 1M citric acid, 2.73M NaOH and 0.01M NaCl was prepared.

The buffered gelatin electrolyte had a pH of approximately 5.5. 200 microliters of the buffer was mixed with 10 ml of the gelatin solution. 1.52 ml of this mixture was solvent cast on the 100-sensor wafer described above, and allowed to evaporate at 80 degrees C.

The chip as described above was further processed as follows. A membrane selective for hydrogen ion was fabricated. A 10% by weight membrane solution was prepared in THF containing 2 weight % tridodecylamine, 0.4 weight % potassium tetrakis (4-chlorophenyl) borate, 65 weight % dioctylphthalate, and 33 weight % PVC. A volume of 1.2 ml of membrane solution was solvent cast onto a 100-sensor wafer. The layer was dried at room temperature in a THF environment for about 24 hours. Final membrane thickness was approximately 40 microns.

The chips were diced, to define a plurality of individual pH sensors.

EXAMPLE 4

Performance of Analyzer pH Sensor

Aqueous samples tonometered with clinical levels of $CO_2$ were measured with high pH precision and accuracy using an analyzer as described in Example 3, with a 130 second stopped-flow protocol. Sensor drifts with $CO_2$ tonometered samples were −0.002 mV/min. Using a 130 second stopped-flow measurement protocol, precisions below 0.008 pH units and accuracies better than 0.02 pH units were achieved. Adequate gas impermeability was demonstrated since pH sample integrity is strongly affected by any $CO_2$ losses through the gasket. Furthermore, no significant deterioration in sensor performance was observed over 30 days of continuous use. This demonstrates excellent chemical compatibility of the fluoroelastomer with the plasticized polymeric sensor membrane.

The preceding examples are set forth to illustrate specific embodiments of the invention and are not intended to limit the scope of the invention. Additional embodiments and advantages within the scope of the claimed invention, for example measuring electroactive species other than the gases and ionic species mentioned above, will be apparent to those of ordinary skill in the art.

What is claimed is:

1. An electrochemical analyzer comprising:
an electrochemical sensor having a surface, a portion of the surface defining a sensing area; and
a sample container which positions a sample at the sensing area, at least a portion of the container defined by an elastomeric fluoropolymer.

2. An electrochemical analyzer as in claim 1, wherein the fluoropolymer comprises a vinylidene fluoride-hexafluoropropylene copolymer.

3. An electrochemical analyzer as in claim 1, wherein the sensor includes a first primary membrane, a portion of which defines the sensing area, and the elastomeric fluoropolymer is contiguous with the first primary membrane.

4. An electrochemical analyzer as in claim 3, further comprising a second electrochemical sensor including a second primary membrane, a portion of which defines a second sensing area, wherein the elastomeric fluoropolymer is contiguous with the second primary membrane.

5. An electrochemical analyzer as in claim 4, wherein the first and second primary membranes each are contacted by a continuous portion of elastomeric fluoropolymer.

6. An electrochemical analyzer as in claim 4, wherein the sample container positions a fluid sample at the sensing area of the first primary membrane and at the second sensing area, the analyzer further comprising an injector which injects a metered dose of fluid sample into the container in an amount essentially no greater than that required for stopped-flow analysis at the first and second sensors.

7. An electrochemical analyzer as in claim 4, further comprising a detection mechanism constructed and arranged to determine a plurality of analytes while a sample is positioned at the sensing area of the first sensor and the sensing area of the second sensor and is prevented from flowing.

8. An electrochemical analyzer as in claim 3, wherein the sample container comprises a cover which receives a fluid sample and the elastomeric fluoropolymer is a gasket between the cover and a sensing surface of the first primary membrane.

9. An electrochemical analyzer as in claim 8, wherein the sensor includes an electrode in electrical communication with a surface of the first primary membrane opposite the sensing surface, and the gasket forms an electrochemical seal between the electrode and the sensing surface.

10. An electrochemical analyzer as in claim 1, wherein the sensor includes a first primary membrane having a first surface in electrical communication with an electrode and a sensing surface opposite the first surface, a portion of which defines in part the sensing area, wherein the elastomeric fluoropolymer forms an electrochemical seal between the electrode and the sensing surface of the first primary membrane.

11. An electrochemical analyzer as in claim 10, wherein the sample container comprises a cover which receives a fluid sample and the elastomeric fluoropolymer is a gasket between the cover and the sensing surface of the first primary membrane.

12. An electrochemical analyzer as in claim 10, further comprising a second electrochemical sensor including a second primary membrane having a first surface in electrical communication with a second electrode and a sensing surface opposite the first surface, a portion of which defines in part a second sensing area, and an elastomeric fluoropolymer that forms an electrochemical seal between the second electrode and the sensing surface of the second primary membrane.

13. An electrochemical analyzer as in claim 12, wherein a continuous portion of an elastomeric fluoropolymer forms the electrochemical seal at the first sensor and the electrochemical seal at the second sensor.

14. An electrochemical analyzer comprising:
an electrochemical sensor having a first primary membrane having a surface, a portion of which defines a sensing area; and a sample container comprising a cover which receives and positions a sample at the sensing area, at least a portion of the container defined by an elastomeric fluoropolymer gasket between the cover and a sensing surface of the first primary membrane and contiguous with the first primary membrane wherein the sensor includes an electrode in electrical communication with a surface of the first primary membrane opposite the sensing surface, and the gasket forms an electrochemical seal providing wet electrical resistance between the electrode and the sensing surface of the first primary membrane via a pathway that circumvents the membrane that is at least twice the wet resistance across the membrane.

15. An electrochemical analyzer as in claim 14, wherein the fluoropolymer comprises a vinylidene fluoride-hexafluoropropylene copolymer.

16. An electrochemical analyzer as in claim 14, further comprising a second electrochemical sensor including a second primary membrane, a portion of which defines a second sensing area, wherein the elastomeric fluoropolymer gasket is contiguous with the second primary membrane.

17. An electrochemical analyzer as in claim 14, wherein the first and second primary membrane each are contacted by a contiguous portion of the elastomeric fluoropolymer gasket.

18. An electrochemical analyzer as in claim 14, further comprising an injector which injects a metered dose of fluid sample into the container in an amount essentially no greater than that required for stop-flow analysis.

19. An electrochemical analyzer comprising:

a first electrochemical sensor constructed and arranged for determining a gas, the first sensor including a first primary membrane having a first sensing area, and a container which positions a sample suspected of containing the gas at the first sensing area and that is defined at least in part by the first primary membrane and an elastomer that is contiguous with the first primary membrane; and a second electrochemical sensor constructed and arranged for determining an ionic species, the second sensor including a second primary membrane having a second sensing area, and a container which positions a sample suspected of containing the ionic species at the second sensing area and that is defined at least in part by the second primary membrane and an elastomer, essentially the same as the elastomer contiguous with the first membrane, that is contiguous with the second primary membrane.

20. An electrochemical analyzer as in claim 19, wherein the elastomer comprises a fluoropolymer.

21. An electrochemical analyzer as in claim 20, wherein the fluoropolymer comprises a vinylidene fluoride-hexafluoropropylene copolymer.

22. An electrochemical analyzer as in claim 19, wherein a continuous portion of an elastomer is contiguous with the first primary membrane and with the second primary membrane.

23. An electrochemical analyzer as in claim 22, wherein the elastomer comprises a fluoropolymer.

24. An electrochemical analyzer as in claim 23, wherein the fluoropolymer comprises a vinylidene fluoride-hexafluoropropylene copolymer.

25. An electrochemical analyzer as in claim 19, wherein the container of the first sensor and the container of the second sensor are continuous, and the elastomers contiguous with the first and second primary membranes comprise gaskets forming fluid seals between a cover which receives a fluid sample and the first and second primary membranes, respectively.

26. An electrochemical analyzer as in claim 19, wherein the first electrochemical sensor includes a first electrode in electrical communication with a surface of the first primary membrane opposite the surface contiguous with the elastomer, and the elastomer forms an electrochemical seal between the first electrode and the surface of the first membrane contiguous with the elastomer, and the second electrochemical sensor includes a second electrode in electrical communication with a surface of the second primary membrane opposite the surface contiguous with the elastomer, the elastomer forming an electrochemical seal between the second electrode and the surface of the second membrane contiguous with the elastomer.

27. An electrochemical analyzer as in claim 26, wherein the wet electrical resistance across the elastomer between the first electrode and the surface of the first primary membrane contiguous with the elastomer is at least about 50 gigaohms, and the electrical resistance across the elastomer between the second electrode and the surface of the second primary membrane contiguous with the elastomer is at least about 50 gigaohms.

28. An electrochemical analyzer as in claim 26, wherein the elastomer comprises a fluoropolymer.

29. An electrochemical analyzer as in claim 28, wherein the fluoropolymer comprises a vinylidene fluoride-hexafluoropropylene copolymer.

30. An electrochemical analyzer as in claim 19, wherein the gas is oxygen or carbon dioxide and the ionic species is sodium ion, potassium ion, chloride ion, or calcium ion.

31. An electrochemical analyzer as in claim 30, wherein the first electrochemical sensor includes the first primary membrane having a first surface in electrical communication with a first electrode and a sensing surface opposite the first surface, a portion of which defines in part the first sensing area, and the second sensor includes the second primary membrane having a first surface in electrical communication with a second electrode and a sensing surface opposite the first surface, a portion of which defines in part the second sensing area, wherein the elastomer forms an electrochemical seal between the first electrode and the sensing surface of the first primary membrane, and forms an electrochemical seal between the second electrode and the sensing surface of the second primary membrane.

32. An electrochemical analyzer as in claim 31, wherein a continuous portion of an elastomer is contiguous with the first primary membrane and with the second primary membrane.

33. An electrochemical analyzer as in claim 32, wherein the elastomer comprises a fluoropolymer.

34. An electrochemical analyzer as in claim 33, wherein the fluoropolymer comprises a vinylidene fluoride-hexafluoropropylene copolymer.

35. An electrochemical analyzer as in claim 19, wherein the sample container positions a fluid sample at the sensing area of the first primary membrane and at the second sensing area, the analyzer further comprising an injector which injects a metered dose of fluid sample into the container in an amount essentially no greater than that required for stopped-flow analysis at the sensing area of the first primary membrane and at the second sensing area.

36. An electrochemical analyzer as in claim 19, further comprising a detection mechanism constructed and arranged to determine a plurality of analytes while a sample is positioned at the sensing area of the first sensor and the sensing area of the second sensor and is prevented from flowing.

37. A method of electrochemical analysis, comprising:

delivering a sample suspected of containing an analyte into an electrochemical analyzer sample container, the sample container defined at least in part by a first primary membrane that is a component of a first electrochemical sensor constructed and arranged for determining a first analyte, a second primary membrane that is a component of a second electrochemical sensor constructed and arranged for determining a second analyte, and an elastomer that is contiguous with the primary membrane of the first sensor;

preventing the sample from flowing; and determining the first analyte while the sample is prevented from flowing.

38. A method as in claim 37, wherein the elastomer comprises a fluoropolymer.

39. A method as in claim 38, wherein the fluoropolymer comprises a vinylidene fluoride-hexafluoropropylene copolymer.

40. A method as in claim 37, wherein a continuous portion of the elastomer is contiguous with the primary membrane of the first sensor and with the primary membrane of the second sensor.

41. A method as in claim 40, wherein the container comprises a cover, and the elastomer is a gasket that is contiguous with the first primary membrane and contiguous with the second primary membrane and forms a fluid seal between the first primary membrane and the cover and between the second primary membrane and the cover.

42. A method as in claim 41, wherein the first primary membrane includes a first surface in electrical communication with a first electrode and a sensing surface opposite the first surface which defines in part the sample container, and the second primary membrane includes a first surface in electrical communication with a second electrode and a sensing surface opposite the first surface which defines in part the sample container, and the elastomer is a gasket that forms an electrochemical seal between the first electrode and the sensing surface of the first primary membrane, and forms an electrochemical seal between the second electrode and the sensing surface of the second primary membrane.

43. A method as in claim 42, wherein the wet resistance across the elastomer between the first electrode and the sensing surface of the first primary membrane is at least about 50 gigaohms.

44. A method as in claim 43, wherein the wet resistance across the elastomer between the second electrode and the sensing surface of the second primary membrane is at least about 50 gigaohms.

45. A method as in claim 42, wherein the gasket comprises an elastomeric fluoropolymer.

46. A method as in claim 45, wherein the gasket comprises a vinylidene fluoride-hexafluoropropylene copolymer.

47. A method as in claim 37, wherein the first analyte is a gas and the second analyte is an ionic species.

48. A method as in claim 47, wherein the gas is oxygen or carbon dioxide and the ionic species is sodium ion, potassium ion, chloride ion, or calcium ion.

49. A method as in claim 47, wherein the elastomer comprises a fluoropolymer.

50. A method as in claim 47, wherein the fluoropolymer comprises a vinylidene fluoride-hexafluoropropylene copolymer.

51. An electrochemical analyzer comprising:

an electrochemical sensor including a heterogeneous membrane having a surface, a portion of the surface which receives a sample for electrochemical analysis; and a sample container which positions a sample at the sensing area, a portion of the sample container comprising an essentially gas-impermeable elastomer contiguous with the heterogeneous membrane.

52. An electrochemical analyzer as in claim 51, wherein the elastomer is a fluoropolymer.

53. An electrochemical analyzer as in claim 52, wherein the fluoropolymer comprises a vinylidene fluoride-hexafluoropropylene copolymer.

54. In an electrochemical analyzer for determining an analyte present in a fluid, the analyzer having a primary sensing membrane positioned to contact the fluid, and having an impermeable container enclosing at least a portion of the membrane, the improvement comprising:

the container being sealed by a sealing fluoroelastomeric gasket.

55. In an electrochemical analyzer as in claim 54, the improvement wherein the gasket is a continuous gasket encircling a portion of the primary membrane defining a sensing surface.

56. In an electrochemical analyzer as in claim 54, the improvement wherein the gasket has a Shore A of between about 10 and about 100.

57. In an electrochemical analyzer as in claim 54, the improvement wherein the permeability of the gasket to carbon dioxide is less than about 100 barrers, or the permeability of the gasket to oxygen is less than about 20 barrers.

58. In an electrochemical analyzer as in claim 54, the improvement wherein the gasket forms a seal through which the passage of fluid and gas is substantially barred such that testing may be carried out for a period of at least two days under normal sensor operation.

59. In an electrochemical analyzer as in claim 54, the improvement wherein the gasket has a Shore A of between about 10 and about 100, a permeability to carbon dioxide of less than about 100 barrers, the gasket forming a seal through which the passage of fluid and gas is substantially barred such that testing may be carried out for a period of at least two days under normal sensor operation.

60. In an electrochemical analyzer as in claim 54, the improvement wherein the analyzer is constructed and arranged for determining a gas or an analyte the determination of which is dependant on gas present in the fluid, and the container is sealed against gas permeability by the gasket.

61. In an electrochemical analyzer for determining an analyte present in a fluid, the analyzer having a primary sensing membrane positioned to contact the fluid, and having an impermeable container enclosing at least a portion of the membrane, the improvement comprising:

the container being sealed by a sealing fluoroelastomeric gasket that forms an electrochemical seal providing wet electrical resistance between an electrode of the analyzer and a sensing surface of the primary membrane via a pathway that circumvents the membrane that is at least twice the wet resistance across the membrane.

62. In an electrochemical analyzer as in claim 61, the improvement wherein the gasket is a continuous gasket encircling a portion of the primary membrane defining a sensing surface.

63. In an electrochemical analyzer as in claim 61, the improvement wherein the gasket has a Shore A of between about 10 and about 100.

64. In an electrochemical analyzer as in claim 61, the improvement wherein the permeability of the gasket to carbon dioxide is less than about 100 barrers, or the permeability of the gasket to oxygen is less than about 20 barrers.

65. In an electrochemical analyzer as in claim 61, the improvement wherein the gasket forms a seal through which the passage of fluid and gas is substantially barred such that testing may be carried out for a period of at least two days under normal sensor operation.

66. In an electrochemical analyzer as in claim 61, the improvement wherein the gasket has a Shore A of between about 10 and about 100, a permeability to carbon dioxide of less than about 100 barrers, the gasket forming a seal through which the passage of fluid and gas is substantially barred such that testing may be carried out for a period of at least two days under normal sensor operation.

67. In an electrochemical analyzer for determining an analyte present in a fluid, the analyzer having a primary sensing membrane positioned to contact the fluid, and having an impermeable container enclosing at least a portion of the membrane, the improvement comprising:

the container being sealed by a sealing fluoroelastomeric gasket having a Shore A of between about 10 and about 100, a permeability to carbon dioxide of less than about 100 barrers, the gasket forming a seal through which the passage of fluid and gas is substantially barred such that testing may be carried out for a period of at least two days under normal sensor operation, the gasket forming an electrochemical seal providing wet electrical resistance between an electrode of the analyzer and a sensing surface of the primary membrane via a pathway that circumvents the membrane that is at least twice the wet resistance across the membrane.

68. In an electrochemical analyzer as in claim 67, the improvement wherein the analyzer is constructed and arranged for determining a gas or an analyte the determination of which is dependant on gas present in the fluid, and the container is sealed against gas permeability by the gasket.

69. An electrochemical analyzer comprising:

an electrochemical sensor having a first primary membrane having a surface, a portion of which defines a sensing area, and an electrode in electrical communication with a surface of the first primary membrane opposite the sensing surface; and a sample container comprising a cover which receives and positions a sample at the sensing area, at least a portion of the container defined by an elastomeric fluoropolymer contiguous with the first primary membrane, wherein the fluoropolymer forms an electrochemical seal providing wet electrical resistance between the electrode and the sensing surface of the first primary membrane via a pathway that circumvents the membrane that is at least twice the wet resistance across the membrane.

70. An electrochemical analyzer as in claim 69, wherein the fluoropolymer comprises a vinylidene fluoride-hexafluoropropylene copolymer.

71. An electrochemical analyzer as in claim 69, further comprising a second electrochemical sensor including a second primary membrane, a portion of which defines a second sensing area, wherein the elastomeric fluoropolymer gasket is contiguous with the second primary membrane.

72. An electrochemical analyzer as in claim 69, wherein the first and second primary membrane each are contacted by a contiguous portion of the elastomeric fluoropolymer gasket.

73. An electrochemical analyzer as in claim 69, further comprising an injector which injects a metered dose of fluid sample into the container in an amount essentially no greater than that required for stop-flow analysis.

74. An electrochemical analyzer as in claim 69, wherein the container includes an inner surface that contacts a fluid sample when a fluid sample is introduced into the sensor, the entire inner surface defining an elastomeric fluoropolymer.

75. An electrochemical analyzer as in claim 69, wherein the entire sample container is made of an elastomeric fluoropolymer.

* * * * *